United States Patent [19]

Chu et al.

[11] Patent Number: 4,983,040

[45] Date of Patent: Jan. 8, 1991

[54] LIGHT SCATTERING AND SPECTROSCOPIC DETECTOR

[75] Inventors: Benjamin Chu, Setauket; Harbans S. Dhadwal, Westbury, both of N.Y.

[73] Assignee: The Research Foundation of State University of New York, Albany, N.Y.

[21] Appl. No.: 267,528

[22] Filed: Nov. 4, 1988

[51] Int. Cl.⁵ .......................................... G01N 21/49
[52] U.S. Cl. .................................. 356/338; 356/339; 356/342
[58] Field of Search ............... 356/338, 339, 340, 342; 250/574

[56] References Cited

U.S. PATENT DOCUMENTS

| | | | |
|---|---|---|---|
| 3,518,437 | 6/1970 | Riggs | 250/574 X |
| 4,471,659 | 9/1984 | Udd et al. | 350/358 X |
| 4,643,573 | 2/1987 | McLachlan et al. | 356/338 |

FOREIGN PATENT DOCUMENTS 8807179 9/1988 PCT Int'l Appl. ................. 356/338

OTHER PUBLICATIONS

Proposal leading to Grant #431-5010D—State University of New York transmittal for applications submitted to sponsor by the campus—F 105-777.
*Dynamic Light Scattering Using Monomode Optical Fibers*, (Brown), Nov. 15, 1987.
*Monomode Fiber Component For Dynamic Light Scattering*, (Brown et al.), Dec. 1987.

Primary Examiner—Davis L. Willis
Assistant Examiner—Matthew W. Koren
Attorney, Agent, or Firm—Hoffmann & Baron

[57] ABSTRACT

A laser light scattering and spectroscopic detector is provided which includes a probe comprising an optical fiber coupled to a graded index microlens. The angular aperture and the divergence of the probe are designed specifically to satisfy the scattering volume and coherence requirements for laser light scattering and spectroscopic measurements. The detector includes a housing which defines an elongate cell therein and a selected number of detector ports extending at various angles with respect to the cell. A method is provided for detecting scattered light which includes the steps of positioning the probe inside or outside the scattering medium at a selected angle with respect to the laser beam.

31 Claims, 4 Drawing Sheets

LIGHT SCATTERING AND SPECTROSCOPIC DETECTOR

BACKGROUND OF THE INVENTION

The field of the invention relates to light scattering apparatus for use in particle sizing, molecular weight determination and other applications.

Conventional light scattering apparatus include relatively bulky optical and mechanical components which do not readily permit remote sensing and process control. Such apparatus often employ a goniometer which is one of the most bulky and expensive components of a light scattering spectrometer.

Back scatter anemometers have been used in the field of dynamic light scattering. These instruments may employ single mode or multimode optical fibers in connection with directional couplers and solid state lasers. The back scatter probe used therewith may be inserted within the scattering medium.

Relatively large optical fibers and optical fiber bundles have been used in light scattering spectrometers. One such spectrometer includes a combination of 1 mm optical fibers, pinholes, lenses and electronic shutters positioned at several different scattering angles, thereby eliminating the need for a goniometer. However, this arrangement is not conducive to miniaturization, and measurements of the scattered light must be made outside the scattering cell.

SUMMARY OF THE INVENTION

It is an object of the invention to provide a fiber optic light scattering spectrometer which can be optimized for static and dynamic light scattering, as well as other forms of light scattering techniques such as Raman spectroscopy.

It is another object of the invention to provide a spectrometer which lends itself to miniaturization and permits remote sensing and process control.

A still further object of the invention is to provide a spectrometer having no moving parts.

In accordance with the above and other objects of the invention, a spectrometer is provided which includes a light scattering cell and one or more fiber optic detector probes inserted within the cell. A method is also provided for detecting scattered light by inserting the detector probe within the scattering medium. This allows the probe to be positioned within an arbitrarily small distance from the incident beam.

An array of detector probes is preferably employed to provide either simultaneous or multiplexed measurements of the scattered light intensity and spectrum at various scattering angles. The probes each comprise an optical fiber and a graded index microlens.

DETAILED DESCRIPTION OF THE INVENTION

A light scattering spectrometer employing fiber optic detector probes secured thereto is provided. Each probe includes an optical fiber and a graded index microlens. The spectrometer has no moving parts, and the probes form integral parts of the scattering cell.

Figure 1:
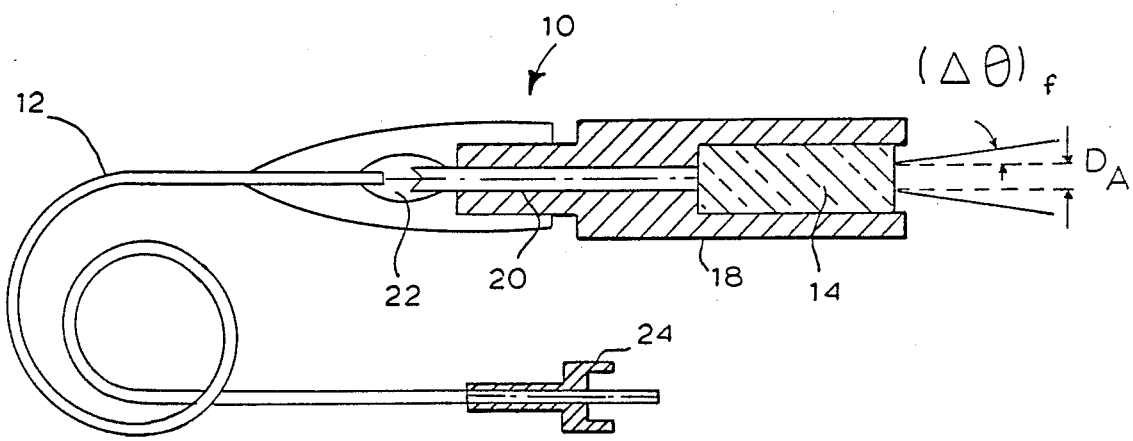
FIG. 1 is a schematic illustration of a fiber optic detector probe used in connection with the invention.

Referring to FIG. 1, a compact fiber optic probe 10 is shown which comprises an optical fiber 12 of the type used in lightwave communications and a graded index, quarter pitch microlens 14. A 1.8 mm graded index microlens having a circular cross section may, for example, be coupled to a multimode fiber having a core diameter of 10 $\mu$m or 50 $\mu$m. A 2 mm graded index microlens may be coupled to a single mode fiber having a core diameter of about 4 $\mu$m. The three probes gave aperture diameters of 0.410 mm, 0.410 mm and 1.3 mm and divergence angles (in air) of 5.0 mrad, 25 mrad and 0.3 mrad, respectively. Multimode fibers are preferred for both static and dynamic measurements of scattered light intensity. The probe may be designed to function as a transmitter and/or a receiver of laser light to and from a remote scattering region. A typical probe is about two mm in diameter fifteen to twenty-five mm in length. This small size allows for considerable miniaturization of the light scattering spectrometer with which it is employed. A total outside diameter of the probe of less than about five mm is particularly preferred. Careful matching of the optical fiber and microlens creates the desired properties of the probe, which can be used either in an imaging configuration or in a non-imaging mode. The latter is chosen to demonstrate its utility for dynamic and/or static light scattering.

Figure 2:
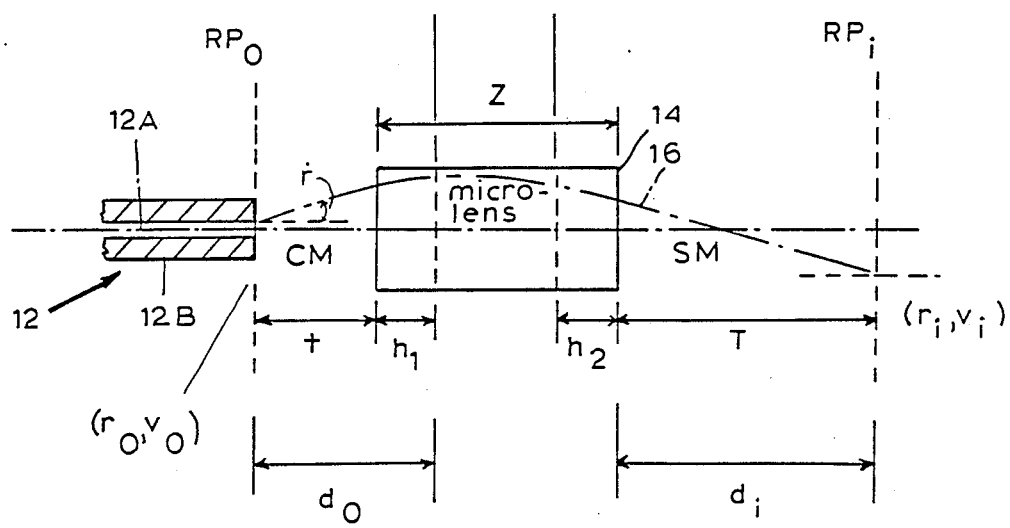
FIG. 2 is a schematic illustration of the fiber optic detector probe including a typical ray path extending therethrough.

Geometrical optics, by means of ray tracing using transfer matrices, are employed as the design tool for describing the propagation of the laser light emanating from the tip of an optical fiber as it propagates through arbitrary stratified media. The propagating ray is defined by two parameters: its height, r at the point of intersection with a reference plane; and angle r which a particular ray makes with the optical axis, as shown in FIG. 2. It is more convenient if the angle r is replaced by the corresponding 'optical direction-cosine' nr (or, strictly speaking $n\sin(r)$) where n is the refractive index of the medium in which the ray is travelling. The optical direction cosine, which shall be denoted by V, has the property that it will remain unchanged as it crosses a plane boundary between two different media. With this notation the propagation of a ray through a series of different media, bounded by parallel planes, can be expressed through the matrix relation $$\begin{bmatrix} r_p \\ v_p \end{bmatrix} = [R_p] \cdot [R_p - 1] \ldots [R_o] \begin{bmatrix} r_o \\ v_o \end{bmatrix}$$

where $$[R_o], \ldots [R_p]$$

are transfer (or ABCD) matrices the first and p'th medium and $[r_p, \nu_p]$ define the ray in a plane bounding the p and p+1 media. With knowledge of the transfer matrices for different types of media, the imaging conditions for an arbitrary optical system can be quickly derived.

FIG. 2 is a schematic illustration of a fiber optic probe. The optical fiber is characterized by a core diameter, $D_f(=2r_o)$ and a numerical aperature, $(NA)_f$ in air. Versatility is introduced in the design stage by having an arbitrary coupling medium between the optical fiber 12 and the microlens 14; and by allowing the output face of the microlens to be embedded into an arbitrary scattering medium. The coupling medium is assumed to be isotropic and homogeneous with a refractive index $n_{cm}$. The scattering medium has a refractive index $n_{sm}$. The ABCD matrix for such a medium is given by $$\begin{bmatrix} 1 & t \\ 0 & 1 \end{bmatrix}$$

where t is the optical path length in the medium. The microlens, a distributed lens-like medium has a radial index profile $n(r) = N_o[1.0 - \frac{1}{2}Ar^2]$. The corresponding ABCD matrix is, $$\begin{bmatrix} \cos(\sqrt{A}\ z) & \frac{1}{N_o\sqrt{A}}\sin(\sqrt{A}\ z) \\ -N_o\sqrt{A}\sin(\sqrt{A}\ z) & \cos(\sqrt{A}\ z) \end{bmatrix}$$

where z is the length of the medium in mm, A is a refractive index gradient constant in mm$^{-2}$, and $N_o$ is the refractive index on the axis. Thus for a general fiber optic probe shown in FIG. 2 the ray parameters of the image plane $[r_i, \nu_i]$ can be related to the ray parameters at the object plane $[r_o, \nu_o]$ through the relation $$\begin{bmatrix} r_i \\ \nu_i \end{bmatrix} = \begin{bmatrix} A & C \\ B & D \end{bmatrix} \cdot \begin{bmatrix} r_o \\ \nu_o \end{bmatrix}$$

where
1. $A = \cos(\sqrt{A}z) - TN_o\sqrt{A}\sin(\sqrt{A}z)$

2. $B = \frac{1}{N_o\sqrt{A}}\sin(\sqrt{A}\ z) + t\cos(\sqrt{A}\ z) +$ $T\cos(\sqrt{A}\ z) - TtN_o\sqrt{A}\sin(\sqrt{A}\ z)$ 3. $C = -N_o\sqrt{A}\sin(\sqrt{A}z)$
4. $D = \cos(\sqrt{A}z) - tN_o\sqrt{A}\sin(\sqrt{A}z)$ where $t = t/n_{cm}$, $T = T/n_{sm}$, the pitch of the microlens is given by $$P = \frac{2\pi}{\sqrt{A}}$$

and the focal length of the microlens is $[N_o\sqrt{A}\sin(\sqrt{A}z)]^{-1}$.

The imaging condition is obtained by considering a point source in the object reference plane $RP_o$, that is $r_o = 0$. The image of a point source will be another point, that is, $r_i = 0$ - requiring that $B = 0$. Re-ordering equation no. 2 gives $$T = \frac{tN_o\sqrt{A}\cos(\sqrt{A}\ z) + \sin(\sqrt{A}\ z)}{[tN_o\sqrt{A}\sin(\sqrt{A}\ z) - \cos(\sqrt{A}\ z)]\ N_o\sqrt{A}} \quad 5.$$

and the magnification, $$m\left(=\frac{r_i}{r_o}\right)$$

is given by $$m = \frac{-(N_o\sqrt{A})^2 \sin(\sqrt{A}\ z)}{N_o\sqrt{A}\ t - \cot(\sqrt{A}\ z)} \quad 6.$$

The above two equations can be used to determine the position and magnification of the image for any optical fiber, microlens, coupling and scattering medium combination. By replacing t by $(d_0 - h_1)$ and T by $(d_i - h_2)$ (see FIG. 2), it can be easily shown that equation no. 5 is consistent with the usual lens formula associated with spherical lenses. As shown in FIG. 2, $h_1$ and $h_2$ are the positions of the principal planes of the microlens as measured from the front and back surfaces, respectively, $$\left(h_1 = h_2 = \frac{1}{N_o}\sqrt{A}\tan(\tfrac{1}{2}\sqrt{A}\ z)\right)$$

for the fiber optic probe according to the invention. A non-imaging configuration, has been used herein, that is the image is at infinity ($T = \infty$). Under this condition, equation 5 gives $$t = \frac{1}{N_o\sqrt{A}\tan(\sqrt{A}\ z)} \quad 7.$$

Substituting equation 7 into equation 4 and using equation 3, the diameter, $D_A$ and divergence, $(\Delta\Theta)_f$ of the collimated beam at any plane parallel to the output face of the microlens can be expressed as follows:

$$D_A = 2r_i = \quad (8.)$$

$$2\left[r_o\cos(\sqrt{A}\ z) - r_oTN_o\sqrt{A}\sin(\sqrt{A}\ z) + \frac{\nu_o}{N_o\sqrt{A}\sin(\sqrt{A}\ z)}\right]$$

$$(\Delta\Theta)_f \frac{|\nu_i|}{n_{sm}} = \frac{r_o N_o\sqrt{A}\sin(\sqrt{A}\ z)}{n_{sm}} \quad 9.$$

Equations 8 and 9 can be simplified considerably if a quarter-pitch microlens is used (z = 0.25P). The equations then reduce to $$D_A = \frac{2\nu_o}{N_o\sqrt{A}} \quad 10.$$

-continued $$(\Delta\Theta)_f = \frac{r_o N_o \sqrt{A}}{n_{sm}} \quad 11.$$

It should be noted that $v_o$ is equivalent to the numerical aperture of the optical fiber in the coupling medium and $$r_o = \frac{D_f}{2}.$$

In addition, an image configuration could have been employed for this fiber optic probe.

A generalized approach to the design of fiber optic probes in accordance with the invention has been provided above. The accuracy between the predicted and measured characteristics, of course, depend upon the accuracy of the governing constants and input parameters.

Referring again to FIG. 2, line 16 indicates a typical ray path through the optical system. The optical fiber 12 includes a core 12A and a cladding 12B. A protective sheath (not shown) may be provided about the cladding to protect the fiber. $RP_o$ and $RP_i$ designate the object and image reference planes, respectively. The principal planes of the microlens 14 as measured from the two end faces thereof are designated by $h_1$ and $h_2$. The object and image distances measured from the principal planes are $d_o$ and $d_i$, respectively. A coupling medium CM may be provided between the end of the optical fiber and the microlens. The opposite end of the microlens 14 is positioned within the scattering medium SM.

The detector probe is characterized by an effective entrance pupil, $D_A$ (FIG. 1) and an angular uncertainty, $(\Delta\Theta)_f$ in air. These parameters can be defined by the following equations $$D_A = \frac{2(NA)_f}{N_o \sqrt{A}} \quad 12.$$

$$(\Delta\Theta)_f = \frac{D_f}{2} N_o \sqrt{A} \quad 13.$$

where $D_f$ and $(NA)_f$ are the core diameter and numerical aperture (in air) of the optical fiber, respectively. The microlens has a quadratic refractive index profile $n(r) = N_o(1 - \frac{1}{2}Ar^2)$ where $N_o$ is the refractive index on the optical axis and A is refractive index gradient constant. Equations 12 and 13 show how by a careful choice of optical fiber and graded index microlens, any fiber optic probe can be designed to suit a particular angular, as well as aperture, requirement. However, for dynamic light scattering, the most important parameter is the divergence angle, which according to equation 13 is proportional to the product of the $N_o\sqrt{A}$ and the radius of the core of the optical fiber. Due to the finite diameter, $D_1$ of the microlens, the smallest value of $D_f$ that could be used is dictated by diffraction. Thus ignoring aberration effects, a lower bound can be imposed on $D_f$:

$$D_f \geq \frac{2.44\lambda_o}{D_1 N_o \sqrt{A}}$$

where $\lambda_o$ is the free space wavelength.

The upper and lower boundaries on $D_f$ may at least theoretically be determined by the following:

$$\frac{2.44\lambda_o}{D_1 N_o \sqrt{A}} < D_f < \frac{\lambda_o \sin^2\Theta}{2(NA)_f + D_1 \cos(\Theta) N_o \sqrt{A}}$$

In practice, the achievable fiber optic probe characteristics are determined by the availability of appropriate components.

The role of the optical fiber in the fiber optic detector probe 10 is three-fold: firstly, to provide a field stop; secondly, to allow remote location of the photodetector; and thirdly, to define the effective probe diameter without having to use an additional aperture stop in front of the microlens. In essence, the fiber optic detector probe described here is a spatial low pass implementation of a more general spatial band pass probe, which could be designed by use of additional optical fibers in the back focal plane of the graded index microlens. The use of the graded index microlens permits miniaturization of the fiber optic probe.

Referring again to FIG. 1, the remaining components of the probe shall be discussed. The probe body 18 which houses the microlens 14 is a generally cylindrical body made from stainless steel or other suitable material. A stainless steel ferrule 20 is used for mounting the bare optical fiber. A mass of glue 22 (e.g. epoxy) holds the fiber within the ferrule, and a heat shrinkable tubing protects the fiber and adjacent ferrule. A male connector 24 is mounted to the end of the fiber opposite the end connected to the probe.

Figure 3:
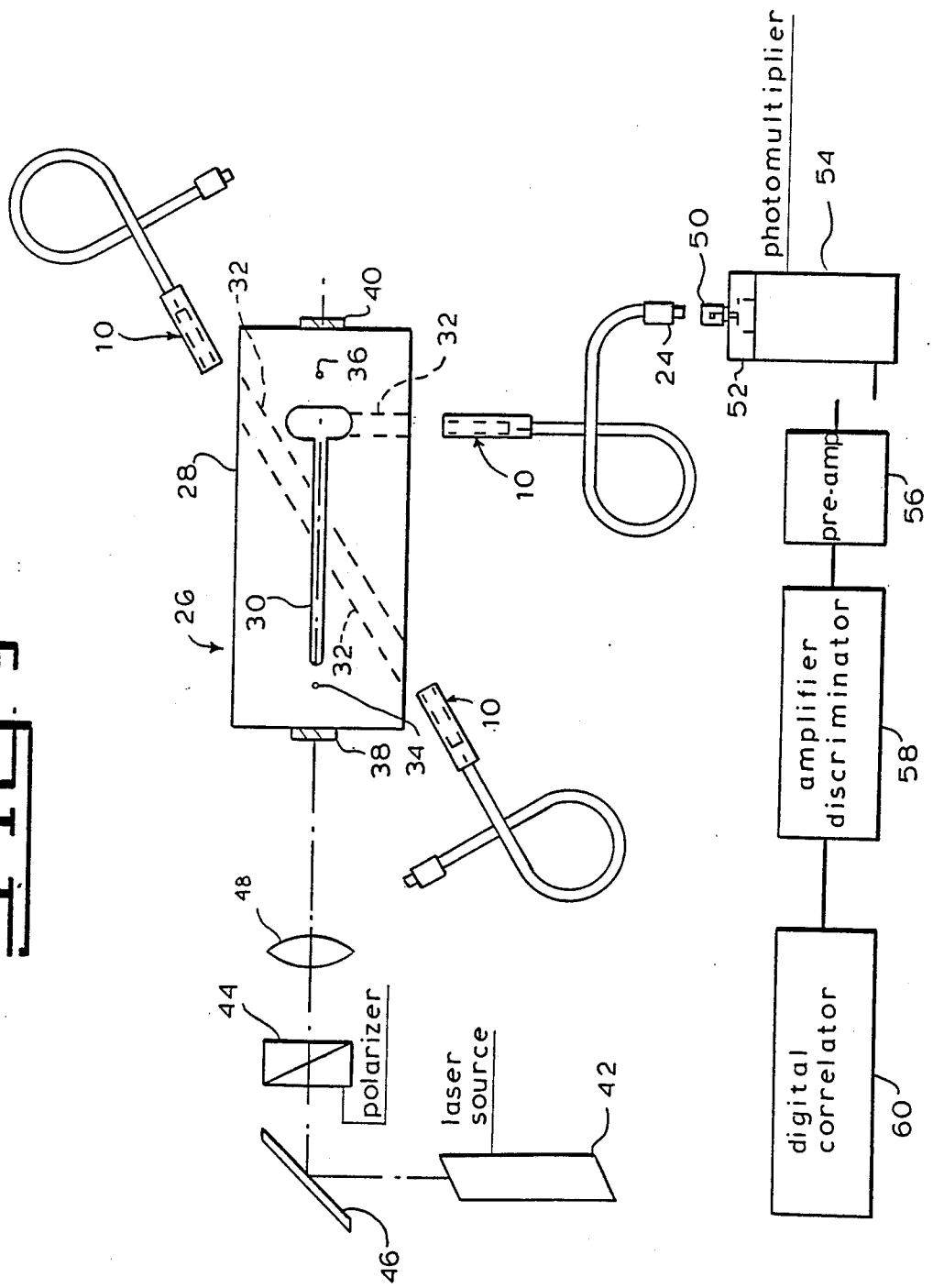
FIG. 3 is a schematic illustration of a spectrometer according to the invention including a plurality of fiber optic detector probes.

FIG. 3 shows a fiber optic light scattering spectrometer 26 and certain other instruments employed therewith. The spectrometer housing is made from two substantially rectangular blocks 28 which are secured together to form a scattering cell 30. The lower of the two stainless steel blocks 28 is shown in the figure. The spectrometer may alternatively be of integral construction and of arbitrary shape with the exception of the probes 10.

The cell 30 as shown in FIG. 3 has a volume of about 0.3 ml. and includes a long, narrow channel to provide access thereto at low (e.g. 2°) and high (e.g. 170°) scattering angles. Three detector ports 32 are shown in FIG. 3 which provide access to 30°, 90°, and 150° scattering angles, respectively. Each port intersects the scattering cell 30 and allows the detector probes 10 to be positioned a small distance from the incident beam, and within the scattering medium. Alternatively, o-ring seals or other mounting techniques could be used.

An inlet port 35 and an outlet port 36 are provided for introducing and removing the scattering medium within the scattering cell. Entrance and exit windows 38, 40 are mounted to the opposite ends of the spectrometer housing.

The incident beam from a laser source (e.g. heliumneon gas laser) 42 is directed to a polarizer 44 by a mirror 46. The beam then passes through a bi-convex lens 48 and into the entrance window 38 of the spectrometer 26. The window 38 may be a one half pitch microlens. In addition, the thick microlens which acts as an entrance window results in a cleaner incident laser beam and also permits a desired focussing of the incident beam into the scattering medium, thereby ensuring plane wave incidence of the correct diameter. A similar construction may be employed for the exit window 40. This window 40 may alternatively be replaced by a small prism for simultaneous measurements of the refractive index of the sample.

The male connector 24 of each detector probe 10 is connected to a female connector 50 of a photomultiplier face plate 52 which comprises a interference filter and a collimating microlens. The remaining elements of the system have conventionally been employed for scattered light analysis, and include a water-cooled thermoelectric photomultiplier tube housing 54 with a photomultiplier tube, a preamplifier 56, an amplifier/discriminator 58, and a digital correlator 60. Since the signals from the optical fibers are processed by using standard optical fiber remote sensing techniques, the above equipment shall not be described in greater detail.

An alternative method for introducing the incident laser beam into the spectrometer would be to employ one of the fiber optic probes for this purpose.

EXAMPLE

A detector probe as shown in FIG. 1 was constructed by combining a single mode fiber having a core diameter of 4 μm and a quarter pitch, graded index microlens. The probe had a divergence angle of 0.3 mrad and an effective aperture ($D_A$) of 1.29 mm. An incident beam from a helium-neon laser was focussed into the center of the spectrometer scattering cell to provide a beam waist diameter of 168 μm. The scattering medium employed was an aqueous suspension of 0.176 μm nominal diameter latex spheres. The concentration was about $10^{-8}$ g/ml. The probe end was inserted into the scattering medium and sequentially positioned in the 30°, 90° and 150° ports. The opposite end of the probe was mounted to the face plate of a water cooled photomultiplier which contained an interference filter and a collimating microlens. A digital correlator was used to measure the intensity-intensity time correlation function.

Figure 4:
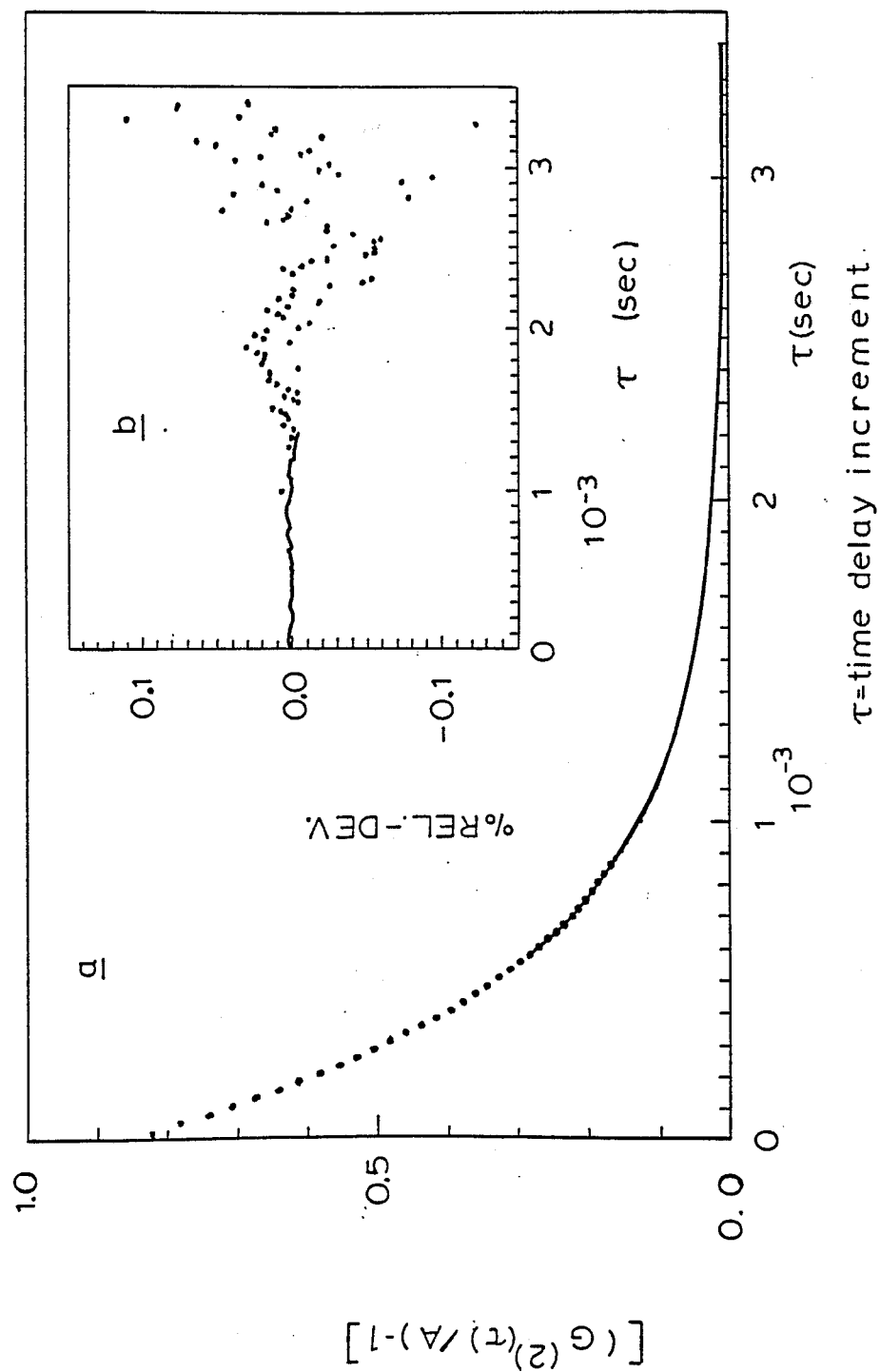
FIG. 4 is a graph illustrating dynamic light scattering measurements using the spectrometer.

Dynamic light scattering measurements using the fiber optic spectrometer described in this example are shown in FIG. 4. Curve (a) is the normalized intensity-intensity time correlation function $$\left[ \frac{\langle G^{(2)}(\tau) \rangle}{A} - 1 \right]$$

obtained using the probe 4 positioned in the 90° detector port shown in FIG. 3. Curve (b) shows the percentage relative deviations, [(data-fit)/fit]×100.

The estimates of particle diameter were within one percent of the expected value, and a variance of 0.03 is also within the error limits associated with unfiltered aqueous suspensions of latex spheres. A high spatial coherence factor ($\beta$) of 0.83 suggests that the spectrometer provides comparable performance to conventional light scattering spectrometers.

The spectrometer provided by the invention fits easily into the palm of the hand, is durable, and is comparatively inexpensive with respect to conventional spectrometers. It is accordingly suitable for industrial use as well as in research laboratories. The small size of the apparatus allows for easy connection with gel permeation chromatography or high pressure liquid chromatography with very small scattering volumes which can be optimized for photon correlation spectroscopy. It also facilitates remote sensing and process control in hostile environments.

Figure 5:
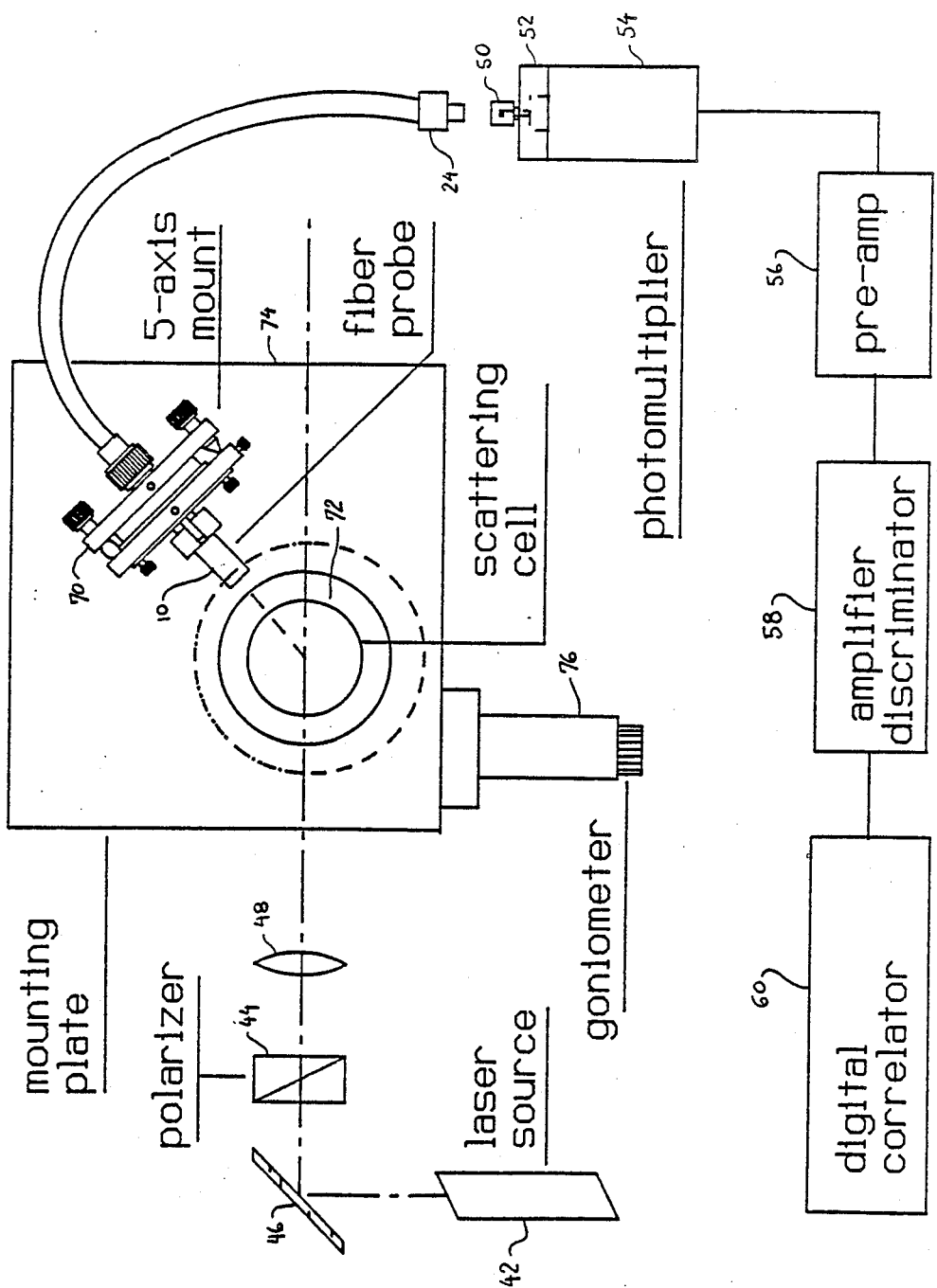
FIG. 5 is a schematic illustration of the detector probe used outside a scattering cell in conjunction with a goniometer.

Referring to FIG. 5, the detector probe 10 may be mounted to a five-axis mount 70. A scattering cell 72 containing a scattering medium is positioned upon a mounting plate 74. The plate is mounted to a gonimeter 76 and is rotatable therewith. The remaining components of the system are the same as those employed in the system shown in FIG. 3. In operation, the probe is positioned in close proximity to the scattering cell. Light scattered by the scattering medium passes through the glass walls of the cell and into the probe. The detected light is then processed in a conventional manner.

What is claimed is:

1. A light scattering and/or spectroscopic detecting apparatus, comprising:
   a housing defining a scattering cell therein;
   means for allowing the passage of a light beam through said scattering cell along an axis;
   an inlet defined within said housing for introducing a fluid medium into said scattering cell;
   at least one detector port extending through said housing and adjoining said scattering cell, said port extending at a scattering angle with respect to said axis; and
   a probe positioned within said port, said probe including an optical fiber and a graded index, quarter pitch microlens coupled to said fiber for gathering light from said scattering cell, whereby
   light directed to said probe from within said scattering cell passes through said graded index microlens and into said optical fiber.

2. An apparatus as defined in claim 1 including a light scattering medium within said scattering cell, said probe extending into said light scattering medium.

3. An apparatus as defined in claim 1 including a plurality of detector ports extending through said housing, each of said ports extending at a different scattering angle with respect to said axis.

4. An apparatus as defined in claim 3 wherein said optical filter is a multimode fiber.

5. An apparatus as defined in claim 1 wherein said microlens is imaged at infinity.

6. An apparatus as defined in claim 1 including means for focussing a light beam within said scattering cell.

7. An apparatus as defined in claim 6 wherein said focussing means is a graded index lens.

8. An apparatus as defined in claim 1 including a laser light source, said means for allowing the passage of a light beam including means for receiving a beam from said laser light source.

9. An apparatus as defined in claim 1 wherein said probe includes a probe body having a substantially cylindrical configuration.

10. An apparatus as defined in claim 9 wherein said probe body has a diameter of less than about five mm.

11. An apparatus as defined in claim 1 wherein said optical fiber includes a core and a cladding about said core.

12. An apparatus for permitting spectroscopic and/or light scattering measurements, comprising;
   a housing defining an elongated cavity therein, said cavity having a longitudinal axis;
   means for allowing the passage of an incident light beam through said cavity;
   a plurality of detector ports extending through said housing and adjoining said cavity, each of said ports extending at a different angle with respect to said axis; and a probe positioned within one of said ports, said probe including an optical fiber and a graded index microlens coupled to said optical fiber, said graded index microlens adjoining said cavity.

13. An apparatus as defined in claim 12 wherein said graded index microlens is imaged at infinity.

14. An apparatus as defined in claim 12 wherein said graded index microlens is a quarter pitch microlens.

15. An apparatus as defined in claim 12 including a laser light source for directing a beam of coherent light to said means for allowing the passage of an incident light beam through said cavity.

16. An apparatus as defined in claim 15 wherein said means for allowing the passage of an incident light beam through said cavity includes a second graded index microlens for focussing said incident beam within said cavity.

17. An apparatus as defined in claim 12 including a fluid medium within said cavity, said graded index microlens being in contact with said fluid medium.

18. An apparatus as defined in claim 12 wherein said optical fiber is a multimode optical fiber.

19. Apparatus as defined in claim 12 wherein said optical fiber is connected to a photodetector at an end of said fiber opposite from said graded index microlens.

20. An apparatus as defined in claim 12 wherein said probe has a cylindrical configuration and a diameter of less then five mm.

21. A method for detecting light from a scattering cell comprising:
providing a scattering cell having a scattering medium contained therein;
passing a light beam through said scattering medium along an axis;
providing a probe including an optical fiber and a graded index, quarter pitch microslens coupled to said optical fiber; and
positioning said probe at a selected angle with respect to said axis such that said light scattered at said angle is received by said graded index, quarter pitch microlens.

22. A method as defined in claim 21 wherein said graded index microlens is positioned adjacent to said axis and within said scattering medium.

23. A method as defined in claim 21 wherein said graded index microlens is positioned adjacent to said cell.

24. A method as defined in claim 21 including the step of focussing said light beam within said scattering medium.

25. A method as defined in claim 21 wherein said optical fiber is a multimode fiber.

26. A method as described in claim 21 including the step of positioning said probe outside said scattering cell.

27. A method as described in claim 21 wherein said optical fiber includes a core and a cladding about said core.

28. A light scattering and/or spectroscopic detecting apparatus, comprising:
a housing defining a scattering cell therein, said scattering cell including an elongated cavity defined by said housing, said elongated cavity including a longitudinal axis;
means for allowing the passage of a light beam through said scattering cell along an axis which is substantially parallel to or collinear with said longitudinal axis of said elongated cavity;
an inlet defined within said housing for introducing a fluid medium into said scattering cell;
at least one detector port extending through said housing and adjoining said scattering cell, said port extending at a scattering angle with respect to said axis; and
a probe positioned within said port, said probe including an optical fiber and a graded index microlens coupled to said fiber for gathering light from said scattering cell, whereby
light directed to said probe from within said scattering cell passes through said graded index microlens and into said optical fiber.

29. A method for detecting light from a scattering cell, comprising:
providing a scattering cell having a scattering medium contained therein;
passing a light beam through said scattering medium along an axis;
providing a probe including a multimode optical fiber and a graded index microlens coupled to said optical fiber; and
positioning said probe at a selected angle with respect to said axis such that said light scattered at said angle is received by said graded index microlens.

30. A method as described in claim 29 including the step of positioning said probe outside said scattering cell.

31. A method as described in claim 29 wherein said optical fiber includes a core and a cladding about said core.

* * * * *